United States Patent [19]

Lee et al.

[11] Patent Number: 4,921,581

[45] Date of Patent: May 1, 1990

[54] EXTRACTIVE DISTILLATION OF HYDROCARBONS EMPLOYING SOLVENT MIXTURE

[75] Inventors: Fu M. Lee; Ronald E. Brown, both of Bartlesville, Okla.

[73] Assignee: Phillips Petroleum Company, Bartlesville, Okla.

[21] Appl. No.: 357,568

[22] Filed: May 26, 1989

[51] Int. Cl.⁵ .................................. B01D 3/40
[52] U.S. Cl. ............................. 203/56; 203/64; 203/65; 203/69; 203/70; 203/DIG. 9
[58] Field of Search ............. 203/65, 56, 63, 64, 203/68, 69, 70, DIG. 9, 91

[56] References Cited

U.S. PATENT DOCUMENTS

| | | | |
|---|---|---|---|
| 2,508,723 | 5/1950 | Mayland et al. | 260/666 |
| 2,679,472 | 5/1954 | Tooke | 202/42 |
| 2,695,322 | 11/1954 | Weedman | 260/666 |
| 2,736,755 | 2/1956 | Reuter et al. | 260/666 |
| 2,771,494 | 11/1956 | Weedman | 260/666 |
| 2,786,804 | 3/1957 | Nelson | 202/42 |
| 2,809,925 | 10/1957 | Nelson | 202/42 |
| 2,839,452 | 6/1958 | Nelson | 202/42 |
| 2,846,485 | 8/1958 | Meason et al. | 260/666 |
| 2,891,894 | 6/1959 | Cier et al. | 202/39.5 |
| 3,034,969 | 5/1962 | Makin, Jr. | 202/39.5 |
| 3,301,911 | 1/1967 | Boatright | 260/666 |
| 3,349,009 | 10/1967 | Ruchlein | 203/67 |
| 3,898,297 | 8/1975 | Sampson et al. | 260/668 A |
| 4,053,369 | 10/1977 | Cines | 203/52 |
| 4,121,978 | 10/1978 | Becuwe | 203/62 |
| 4,141,938 | 2/1979 | Klose | 260/928 |
| 4,230,638 | 10/1980 | Murtha | 203/43 |
| 4,498,980 | 2/1985 | Forte | 208/321 |
| 4,514,262 | 4/1985 | Berg | 203/56 |
| 4,690,733 | 9/1987 | Forte et al. | 203/96 |

OTHER PUBLICATIONS

"Extrative Distillation Saves Energy", by Ian Sucksmith, Chemical Engineering, Jun. 29, 1987, pp. 91–95.
"Handbook of Separation Techniques for Chem. Engineers", by Philip Schweitze, McGraw Hill Book Co., 1979, pp. 1–135 & 1–143.
"Perry's Chemical Engineers' Handbook", 6th Edition, McGraw Hill Book Co., 1984, pp. 13–53 to 13–57.

Primary Examiner—Virginia Manoharan
Attorney, Agent, or Firm—K. K. Brandes

[57] ABSTRACT

An extractive distillation process for separating at least one cycloalkane from at least one close-boiling alkane employs as solvent a mixture of (a) at least one saturated C5–C9 alcohol (preferably cyclohexanol) and (b) at least one glycol compound (preferably tetraethylene glycol).

17 Claims, 1 Drawing Sheet

EXTRACTIVE DISTILLATION OF HYDROCARBONS EMPLOYING SOLVENT MIXTURE

BACKGROUND OF THE INVENTION

In one aspect, this invention relates to the separation of saturated cycloaliphatic hydrocarbons (cycloalkanes, naphthenes) from close-boiling paraffinic hydrocarbons (alkanes, paraffins) by extractive distillation. In another aspect, this invention relates to the use of a mixture of organic hydroxyl compounds as solvent (also referred to as extractant or entrainer) in the aforementioned extractive distillation.

Extractive distillation is a well known technique for separating mixtures of components having such low relative volatility (i.e., having nearly equal volatility and having nearly the same boiling point) that it is difficult to separate these components by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91-95, the disclosure of which is herein incorporated by reference. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers' Handbook, 6th Edition, McGraw-Hill Book Company, 1984, pages 13-53 to 13-57, the disclosures of which are herein incorporated by reference.

The separation of naphthenes (cycloparaffins), in particular cyclohexane, from close-boiling paraffins by extractive distillation is known and has been described in the patent literature, such as in U.S. Pat. Nos. 2,508,723; 2,771,494; 2,846,485; 2,891,894; 3,034,969 and 4,053,369, the disclosure of which are herein incorporated by reference. However, there is an ever present need to develop more selective solvents than those presently known in the extractive distillation of mixtures of close-boiling paraffins and naphthenes. In particular, it is highly desirable to develop improved extractive distillation processes for producing cyclohexane of high purity, which is a starting material for making nylon and other useful polymeric materials.

SUMMARY OF THE INVENTION

It is an object of this invention to provide a process for separating mixtures of close-boiling naphthenes (cycloalkanes) and paraffins (alkanes) by extractive distillation employing a mixture of organic hydroxyl compounds as solvent. It is another object of this invention to produce cyclohexane of high purity from a mixture comprising cyclohexane and close-boiling isoparaffins (i.e., isoparaffins having nearly the same volatility as cyclohexane) by extractive distillation employing a mixture of organic hydroxyl compounds as solvent. It is a further object of this invention to provide a novel mixture of organic hydroxyl compounds. Other objects and advantages will be apparent from the detailed description of the invention and the appended claims.

In accordance with this invention, in a process for separating at least one cycloalkane (naphthene) containing 5-10 carbon atoms per molecule from at least one close-boiling alkane (paraffin), i.e., one alkane or a plurality of alkanes having nearly the same boiling point at atmospheric pressure conditions as said cycloalkane, by extractive distillation of a feed comprising said at least one cycloalkane and said at least one alkane, the improvement comprises using as solvent (also referred to as extractant or entrainer) a mixture of (a) at least one saturated alcohol (alkanol and/or cycloalkanol) containing 5-9 carbon atoms and 1 OH group per molecule and (b) at least one glycol compound having the general chemical formula of

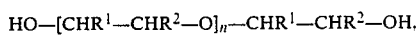

wherein n can be 0, 1, 2, 3, or 4, and $R^1$ and $R^2$ can be independently selected from the group consisting of hydrogen and the methyl group.

In a preferred embodiment, the feed cycloalkane is cyclohexane. In another preferred embodiment, the alcohol component (a) of the solvent is cyclohexanol, and $R^1$ and $R^2$ in the formula of the glycol compound (b) are both H. In a particularly preferred embodiment, said glycol compound is tetraethylene glycol, $HO-[CH_2-CH_2-O]_3-CH_2-CH_2-OH$. In a more preferred embodiment, the solvent consists essentially of (a) and (b).

DETAILED DESCRIPTION OF THE INVENTION

Figure 1:
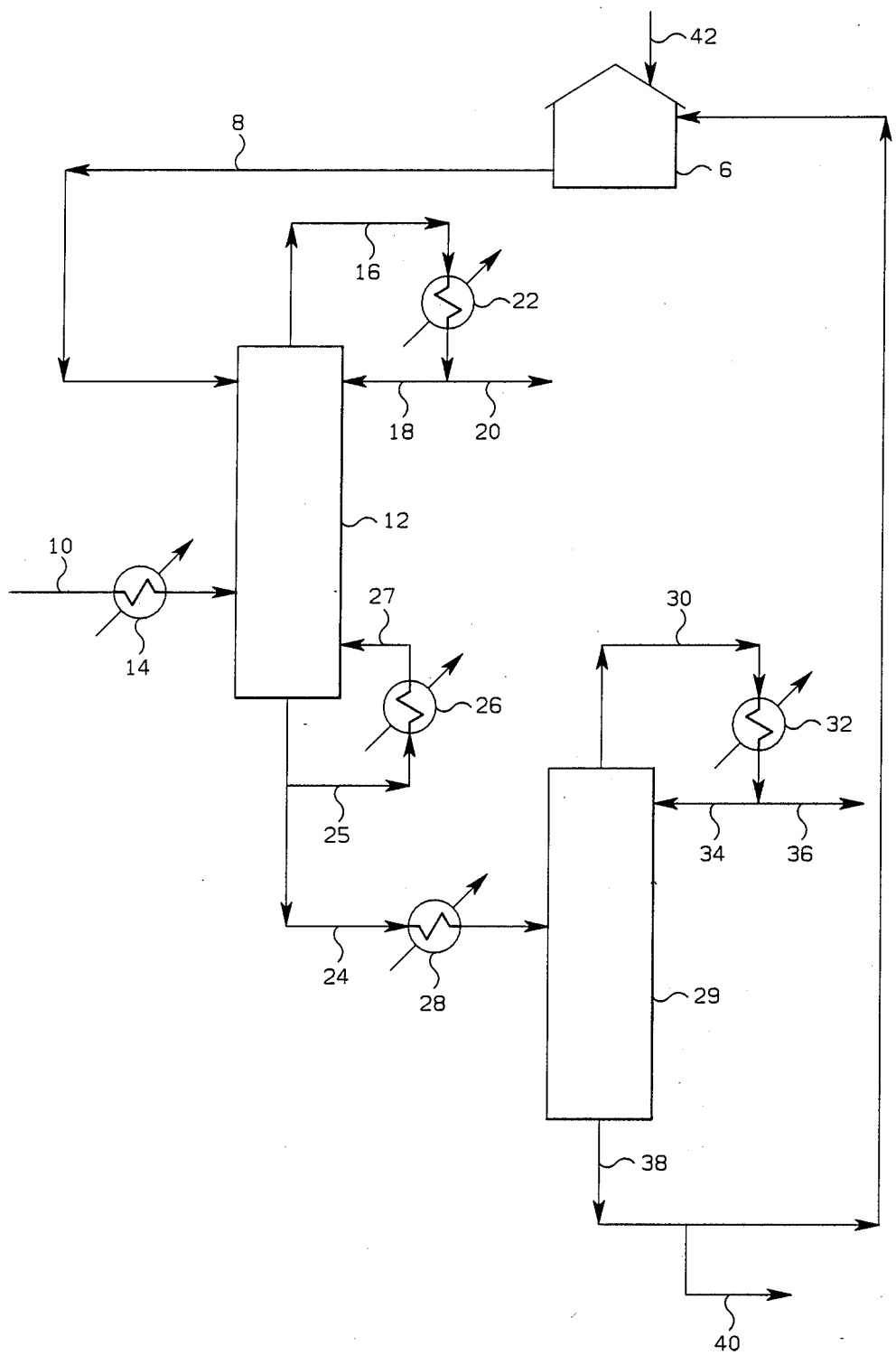
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity.

Any hydrocarbon feed which contains at least one cycloalkane (naphthene) containing 5-9 carbon atoms per molecule and at least one close-boiling alkane (preferably containing 5-10 carbon atoms per molecule, more preferably branched alkane or isoparaffin) can be used in the process of this invention. Preferably, the boiling point (at atmospheric pressure conditions, i.e., about 1 atm.) of the cycloalkane(s) and alkane(s) to be separated by extractive distillation is in the range of from about 80° to about 350° F., more preferably about 100°–300° F. Generally, the boiling points of the cycloalkane(s) and the alkane(s) differ by about 0.2°–10° F. (preferably about 0.5°–5° F.), at about 1 atm.

Non-limiting examples of suitable feed cycloalkanes are cyclopentane, cyclohexane, methylcyclopentane, cycloheptane, 1,1-dimethylcyclopentane, 1,2-dimethylcyclopentane, 1,3-dimethylcyclopentane, ethylcyclopentane, methylcyclohexane, 1,1-dimethylcyclohexane, 1,2-dimethylcyclohexane, 1,3-dmethylcyclohexane, ethylcyclohexane, cyclooctane, and the like, and mixtures thereof. Presently preferred is cyclohexane.

Non-limiting examples of suitable feed alkanes are n-pentane, n-hexane, 2-methylpentane, 3-methylpentane, n-heptane, 2,2-dimethylpentane, 2,4-dimethylpentane, 3,3-dimethylpentane, 2,3-dimethylpentane, 2-methylhexane, 3-methylhexane, 2,2,3-trimethylbutane, n-octane, 2-methyloctane, n-nonane, and the like, and mixture thereof.

Non-limiting examples of alcohols which are suitable as component (a) of the solvent are cyclopentanol, 2-methylcyclopentanol, 3-methylcyclopentanol, cyclohexanol (preferred), 2-methylcyclohexanol, 3-methylcyclohexanol, 2,3-dimethylcyclohexanol, cycloheptanol, 2-methylcycloheptanol, 3-methylcycloheptanol, 4-methylcycloheptanol, 2,3-dimethylcycloheptanol, n-hexanol, 2-methyl-1-hexanol, 3-methyl-1-hexanol, 3-methyl-2-hexanol, n-heptanol, 2-methyl-1-heptanol, 3-methyl-1-heptanol, 3-methyl-2-heptanol, 2,3-dimethyl-1-heptanol, n-octanol, and the like, and mixtures thereof.

Non-limiting examples of glycol compounds include ethylene glycol, isopropylene glycol, 1,2-dimethylethylene glycol, diethylene glycol, diisopropylene glycol, bis(1,2-dimethylene) glycol, triethylene glycol, triisopropylene glycol, tetraethylene glycol (preferred), tetraisopropylene glycol, pentaethylene glycol, pentaisopropylene glycol, and the like, and mixtures thereof.

Any suitable weight ratio of component (b) to component (a) in the solvent (also called extractant) of this invention can be employed in the extractive distillation process of this invention. Preferably, the weight ratio of component (b) to component (a) is in the range of from about 0.2:1 to about 30:1, more preferably from about 1:1 to about 10:1. The preferred component (a) is cyclohexanol, and the preferred component (b) is tetraethylene glycol.

Any suitable weight ratio of the solvent to the hydrocarbon containing feed mixture can be employed. Preferably, the solvent to feed weight ratio is in the range of from about 0.5:1 to about 50:1, more preferably from about 3:1 to about 20:1.

Any suitable reflux ratio (i.e., the weight ratio of the portion of condensed vapor which is returned to the distillation column to the portion of condensed vapor which is withdrawn as distillate) can be employed in the process of this invention. Generally the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the packed column), preferably in the range of from about 70 to about 99 percent, more preferably in the range of from about 80 to about 99 percent.

Any suitable temperature in the distillation vessel (containing primarily the higher boiling feed components and the solvent) can be employed. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exists into the condenser is in the range of from about 100° to about 300° F., preferably in the range of from about 150° to about 250° F. Solvent and feed are generally preheated (generally to a temperature close to the column temperature of the corresponding entry point) before they are introduced into the packed column. Any suitable pressure can be employed during the extractive distillation. Generally the pressure is about 5 to about 100 psig, preferably about 8 to about 20 psig.

Generally, the overhead product (withdrawn from the top of the column) contains a smaller volume percentage of cycloalkanes (preferably cyclohexane) than the feed and a larger volume percentage of alkanes (preferably isoalkanes) than the feed. Generally, the bottoms product (a portion of which can be reheated and recycled to the lower portion of the column) contains more of the cycloalkanes than the feed, and less of the alkanes (preferably isoalkanes) than the feed. Furthermore, the bottom product contains substantially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the cycloalkane product, and the like, and can be determined by those having ordinary skills in the art.

The invention can be better understood by reference to FIG. 1 and the following description of a preferred embodiment of the invention. The feed mixture comprising naphthenic and paraffinic hydrocarbons is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in paraffinic hydrocarbons (alkanes) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottom product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in paraffinic hydrocarbons and a bottoms stream predominantly comprising the naphthenic hydrocarbons and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising naphthenic hydrocarbons is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., naphthenic compounds (preferably cyclohexane) of high purity (preferably higher than 95%), through conduit 36.

A bottom stream predominantly comprising the solvent is withdrawn from a lower portion of distillation column 29 through conduit 38. A portion of this bottoms stream is preferably routed back to solvent storage 6 and then recycled to distillation column 12, while another portion of the bottom stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate the invention and are not to be considered unduly limiting the scope of this invention.

EXAMPLE I

This example demonstrates the superiority as extractant of a mixture of tetraethylene glycol and cyclohexanol versus each component alone.

To a hydrocarbon mixture of 85 weight percent cyclohexane and 15 weight percent 2,3-dimethylpentane (2,3-DMP) was added an extractive solvent (either cyclohexanol or a glycol compound or a mixture of the above) at a solvent:feed weight ratio of 7:1. The total mixture (including the extractive solvent) was heated under reflux conditions for about 20–30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of 2,3-DMP and cyclohexane in the liquid phase and in the condensed vapor phase were determined. The relative volatility R was calculated as follows:

$$R = \frac{Y1/Y2}{X1/X2} = \frac{Y1/X1}{Y2/X2}$$

wherein Y1 and Y2 are the mole fractions of 2,3-DMP and cyclohexane respectively, in the vapor phase, and X1 and X2 are the mole fractions of 2,3-DMP and cyclohexane, respectively, in the liquid phase. Test results are summarized in Table I.

TABLE I

| Added Solvent | Relative Volatility R |
| --- | --- |
| Cyclohexanol | 1.04[4] |
| Ethylene Glycol | 1.02[4] |
| Mixture[1] of Cyclohexanol + Ethylene Glycol | 1.13 |
| Mixture[2] of Cyclohexanol + Ethylene Glycol | 1.22 |
| Tetraethylene Glycol | 1.10[4] |
| Mixture[3] of Cyclohexanol + Tetraethylene Glycol | 1.22 |

[1] 1 part by weight of cyclohexanol and 1 part by weight of ethylene glycol.
[2] 1 part by weight of cyclohexanol and 3 parts by weight of ethylene glycol.
[3] 1 part by weight of cyclohexanol and 3 parts by weight of tetraethylene glycol.
[4] two liquid phases were present in these runs; the other runs contained only one liquid phase.

Test data in Table I clearly show that the mixtures of cyclohexanol and a glycol compound gave higher relative volatility data, and thus are expected to be more effective as solvents (extractants) in the separation of a cycloalkane from isoalkane(s) than either cyclohexanol or the glycol compound alone.

EXAMPLE II

This example illustrates the extractive distillation of a mixture comprising chiefly cyclohexane and minor amounts of isoheptanes (about 10 weight %) in a pilot plant scale extractive distillation setup very similar to the one shown in FIGURE 1 and described above. The composition of a typical feedstock used in these pilot plant scale extractive distillation tests is shown in Table II.

TABLE II

| Feed Component | Wt. % | Boil. Pt. (°F.) |
| --- | --- | --- |
| Cyclohexane | 89.15 | 177.3 |
| 2,2-Dimethylpentane | 1.28 | 174.5 |
| 2,4-Dimethylpentane | 4.00 | 176.9 |
| 2,2,3-Trimethylbutane | 0.81 | 177.6 |
| 3,3-Dimethylpentane | 0.10 | 186.9 |
| 2,3-Dimethylpentane | 0.90 | 193.6 |
| 2-Methylhexane | 1.60 | 194.0 |
| 3-Methylhexane | 1.06 | 197.6 |
| 1,1-Dimethycyclopentane | 0.47 | 190.7 |
| trans 1,3-dimethylcyclopentane (DMCP) | 0.20 | 197.7 |
| cis-1,3-DMCP + trans 1,2-DMCP | 0.26 | 197.9 |
| n-Heptane | 0.08 | 209.1 |
| Others | 0.08 | |
| Total | 100.00 | |

Referring to FIG. 1, the pilot distillation column 12 (inner diameter: 6 inches) was packed with a 8⅓ ft. high layer of one-quarter inch protruded stainless steel particles. During a normal run, the hydrocarbon feed mixture was introduced to the distillation column 12 at a point which was about 25% from the bottom of the packing. The pressure in distillation column 12 was maintained at about 10 psig and the temperature of the feed mixture was maintained slightly above the bubble point of the mixture by manipulating heat exchanger 14. Lean solvent, at a temperature of about 225° F., was fed to distillation column 12 at a point that was about 11% from the top of the packing. An overhead stream enriched in 2,4-dimethylpentane, 2-methylhexane, 2,2-dimethylpentane and other aliphatic components listed in Table II and containing less cyclohexane than the feed, was withdrawn from an upper portion of distillation column 12 through conduit 16 and condensed in condenser 22. Some of the condensed overhead stream was returned to the upper portion of distillation column 12 through conduit 18 as reflux, while the remainder of the condensed overhead stream was returned to a products storage tank through conduit 20.

A bottoms stream predominantly comprising cyclohexane and solvent was withdrawn from a lower portion of distillation column 12 through conduit 24 and then introduced to distillation column 29. The bottoms stream was preheated to the appropriate temperature for introduction to distillation column 29 by adding heat from heat exchanger 28. Distillation column 29 was normally operated at 2 psig, except in runs employing a solvent composition of 90% tetraethylene glycol and 10% cyclohexanol, operating at a pressure of 0.66 psi absolute. An overhead stream predominantly comprising cyclohexane was withdrawn from an upper portion of distillation column 29 through conduit 30 and condensed in condenser 32. A portion of the condensed overhead was returned to an upper portion of distillation column 29 through conduit 34 as a reflux while the remainder was withdrawn through conduit 36. About 4 units of condensed overhead was returned as reflux for every one unit of overhead removed through conduit 36. A portion of the bottoms stream predominantly comprising solvent was returned to solvent storage 6, while another portion was heated in a reboiler (not shown) and returned to the lower portion of column 29.

EXAMPLE III

Various experimental runs were conducted in the pilot plant apparatus, described above, to determine the effect of the solvent to hydrocarbon feed mixture weight ratio, the effect of the reflux ratio and other process parameters.

A summary of the results for the experimental runs to determine the effect of solvent to hydrocarbon feed weight ratio (S/F) is given in Table III below. During these experiments, the amount of reflux returned through conduit 18 was adjusted such that the ratio of the weight of solvent actually in distillation column 12 to the weight of hydrocarbons actually in distillation column 12 remained constant at 7:1. The feed was essentially the same as the one described in Example I, and the solvent contained 75 weight-% tetraethylene glycol and 25 weight-% cyclohexanol.

TABLE III

| Solvent:Feed Weight Ratio | Cyclohexane Purity (Wt. %) | Cyclohexane Recovery (Wt. %) |
|---|---|---|
| 9.3:1 | 97.0 | 52 |
| 12.1:1 | 98.0 | 73 |

TABLE III-continued

| Solvent:Feed Weight Ratio | Cyclohexane Purity (Wt. %) | Cyclohexane Recovery (Wt. %) |
|---|---|---|
| 15.8:1 | 98.1 | 85 |
| 18.0:1 | 98.2 | 90 |

Test data in Table III indicate that a high solvent to feed ratio resulted in a desirably higher combination of cyclohexane purity (weight-% cyclohexane in the bottoms product) and cyclohexane recovery.

Test results summarized in Table IV (below) show the effect of the solvent composition (weight ratio of tetraethylene glycol to cyclohexanol; abbreviated TTEG:CHOL) on cyclohexane purity and recovery, at a constant reflux ratio and a constant solvent:feed ratio.

TABLE IV

| Solvent Composition (TTEG/CHOL) | Cyclohexane Purity (Wt. %) | Cyclohexane Recovery (Wt. %) |
|---|---|---|
| 70/30 | 99.2 | 89.4 |
| 75/25 | 99.2 | 91.7; 93.8 |
| 90/10 | 99.2 | 91.5; 94.2 |

Test results in Table IV indicate that a 90:10 to 75:25 weight ratio of tetraethylene glycol to cyclohexanol was the optimal solvent composition range for attaining maximum cyclohexane purity and recovery.

Test results summarized in Table V (below) show the beneficial effect of a high reflux ratio on cyclohexane purity and recovery, at a constant solvent to feed ratio of about 16:1 and a constant solvent composition (75 weight percent tetraethylene and 25 weight-% cyclohexanol).

TABLE V

| Reflux Weight Ratio (Reflux/Distillate) | Cyclohexane Purity (Wt. %) | Cyclohexane Recovery (Wt. %) |
|---|---|---|
| 1.6 | 97.6 | 83.0 |
| 2.8 | 98.0 | 82.1 |
| 3.6 | 98.2 | 82.0 |
| 5.1 | 98.1 | 83.8 |
| 7.3 | 98.0 | 85.9 |
| 8.9 | 98.0 | 85.6 |
| 14.1 | 97.8 | 87.4 |

Test results in Table VI (below) show that the optimal feed entry point for maximum cyclohexane purity and recovery was about 28% from the bottom of the column.

TABLE VI

| Feed Location (% from Bottom) | Cyclohexane Recovery (Wt. %) | Cyclohexane Purity (Wt. %) |
|---|---|---|
| 10.0 | 90.0 | 98.9 |
| 27.5 | 91.7 | 99.2 |
| 38.8 | 89.6 | 99.0 |

Reasonable variations, modifications and adaptations for various usages and conditions can be made within the scope of the disclosure and the appended claims, without departing from the scope of this invention.

That which is claimed is:

1. In a process for separating at least one cycloalkane containing 5–10 carbon atoms per molecule from at least one close-boiling alkane by extractive distillation of a feed comprising said at least one cycloalkane and said at least one alkane, the improvement which comprises employing a solvent consisting essentially of
(a) at least one saturated alcohol selected from the group consisting of alkanols and cycloalkanols, wherein said alcohol contains 5–9 carbon atoms and one OH group per molecule, and
(b) at least one glycol compound having the general chemical formula of $$HO-[CHR^1-CHR^2-O]_n-CHR^1-CHR^2-OH,$$

wherein n can be 0, 1, 2, 3 or 4, and $R^1$ and $R^2$ are independently selected from the group consisting of hydrogen and a methyl group;
wherein said process produces (i) an overhead product which contains a smaller volume percentage of said at least one cycloalkane and a larger volume percentge of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

2. The process in accordance with claim 1, wherein component (a) of said solvent is cyclohexanol and component (b) of said solvent is selected from the group consisting of ethylene glycol, diethylene glycol, triethylene glycol, tetraethylene glycol and pentaethylene glycol.

3. The process in accordance with claim 2, wherein said component (b) of said solvent is tetraethylene glycol.

4. The process in accordance with claim 1, wherein said at least one cycloalkane in the feed is cyclohexane and said at least one close-boiling alkane is isoalkane.

5. The process in accordance with claim 1, wherein the weight ratio of component (b) to component (a) in said solvent is in the range of from about 0.2:1 to about 30:1.

6. The process in accordance with claim 5, wherein said weight ratio of component (b) to component (a) is in the range of from about 1:1 to about 10:1.

7. The process in accordance with claim 1, wherein said at least one cycloalkane in said feed is cyclohexane, component (a) in said solvent is cyclohexanol, component (b) in said solvent is selected from the group consisting of ethylene glycol, diethylene glycol, triethylene glycol, tetraethylene glycol and pentaethylene glycol, and the weight ratio of component (b) to component (a) in said solvent is in the range of from about 0.2:1 to about 30:1.

8. The process in accordance with claim 7, wherein said weight ratio of component (b) to component (a) is in the range of from about 1:1 to about 10:1.

9. The process in accordance with claim 7, wherein said component (b) in said solvent is tetraethylene glycol.

10. The process in accordance with claim 7, wherein said component (b) in said solvent is tetraethylene glycol, and said weight ratio of component (b) to component (a) is in the range of from about 1:1 to about 10:1.

11. The process in accordance with claim 1, wherein the weight ratio of said solvent to said feed is in the range of from about 0.5:1 to about 50:1.

12. The process in accordance with claim 1, wherein said feed boils at a temperature in the range of from about 80° F. to about 350° F., at a pressure of about 1 atm.

13. The process in accordance with claim 1, wherein the boiling point of said at least one cycloalkane and the boiling point of said at least one alkane differ by about 0.2 to about 10° F., at a pressure of about 1 atm.

14. The process in accordance with claim 1, wherein said at least one cycloalkane in said feed is cyclopentane, component (a) in said solvent is cyclohexanol, component (b) in said solvent is selected from the group consisting of ethylene glycol, diethylene glycol, triethylene glycol, tetraethylene glycol and pentaethylene glycol, and the weight ratio of component (b) to component (a) in said solvent is in the range of from about 0.2:1 to about 30:1.

15. The process in accordance with claim 14, wherein said component (b) in said solvent is tetraethylene glycol.

16. The process in accordance with claim 1, wherein said at least one cycloalkane is cyclohexane.

17. The process in accordance with claim 1, wherein said at least one cycloalkane is cyclopentane.

* * * * *